(12) United States Patent
Harvey et al.

(10) Patent No.: US 9,938,214 B1
(45) Date of Patent: Apr. 10, 2018

(54) RENEWABLE PLASTICIZER ALCOHOLS FROM OLEFIN OLIGOMERS AND METHODS FOR MAKING THE SAME

(71) Applicant: The United States of America, as Represented by the Secretary of the Navy, Washington, DC (US)

(72) Inventors: Benjamin G. Harvey, Ridgecrest, CA (US); Heather A. Meylemans, Ridgecrest, CA (US); Roxanne L. Quintana, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 262 days.

(21) Appl. No.: 14/847,245

(22) Filed: Sep. 8, 2015

Related U.S. Application Data

(62) Division of application No. 13/605,478, filed on Sep. 6, 2012, now abandoned.

(60) Provisional application No. 61/563,168, filed on Nov. 23, 2011.

(51) Int. Cl.
  *C07C 29/149* (2006.01)
  *C07C 2/34* (2006.01)
  *C07C 31/02* (2006.01)

(52) U.S. Cl.
  CPC .............. *C07C 29/149* (2013.01); *C07C 2/34* (2013.01); *C07C 31/02* (2013.01); *C07C 2531/14* (2013.01); *C07C 2531/22* (2013.01)

(58) Field of Classification Search
  None
  See application file for complete search history.

(56) References Cited

U.S. PATENT DOCUMENTS

| | | | | |
|---|---|---|---|---|
| 5,994,278 | A | * | 11/1999 | Duncan ................... C10L 1/143 508/202 |
| 2007/0118007 | A1 | | 5/2007 | Fong et al. |
| 2009/0299109 | A1 | | 12/2009 | Gruber et al. |
| 2010/0160506 | A1 | * | 6/2010 | Wu ...................... C07D 317/36 524/114 |

* cited by examiner

*Primary Examiner* — Pancham Bakshi
*Assistant Examiner* — Mark R Luderer
(74) *Attorney, Agent, or Firm* — Charlene A. Haley

(57) ABSTRACT

An efficient, low-temperature process to convert well-defined olefin oligomers, particularly butene oligomers to branched chain alcohols suitable for use as precursors to plasticizers commonly used in industry, and more specifically, the olefin feedstocks can be conveniently and renewably produced from short chain alcohols.

17 Claims, No Drawings

RENEWABLE PLASTICIZER ALCOHOLS FROM OLEFIN OLIGOMERS AND METHODS FOR MAKING THE SAME

CROSS-REFERENCE TO RELATED APPLICATIONS

This is a divisional patent application claiming the benefit of parent application Ser. No. 13/605,478 filed on Sep. 6, 2012, which is a non-provisional patent application of, claiming the benefit of, parent application Ser. No. 61/563,168 filed on Nov. 23, 2011, and is a continuation-in-part of, claiming the benefit of, parent application Ser. No. 12/511,796 filed on Jul. 29, 2009, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to an efficient, low-temperature process to convert well-defined olefin oligomers, particularly butene oligomers to branched chain alcohols suitable for use as precursors to plasticizers commonly used in industry, and more specifically, the olefin feedstocks can be conveniently and renewably produced from short chain alcohols.

DETAILED DESCRIPTION OF THE EMBODIMENTS OF THE INVENTION

The invention generally relates to an efficient, low-temperature process to convert well-defined olefin oligomers, particularly butene oligomers to branched chain alcohols suitable for use as precursors to plasticizers commonly used in industry, and more specifically, the olefin feedstocks can be conveniently and renewably produced from short chain alcohols.

Plasticizers are widely used in numerous applications to improve the flexibility and durability of plastics and composites. The most important and widely used industrial plasticizer is bis (2-ethylhexyl) phthalate (DEHP) which is produced from 2-ethyl-1-hexanol (2EH) and phthalic anhydride. 2EH is produced on a >2.5 Mton per year scale and is primarily synthesized from propene via hydroformylation to butyraldehyde followed by an aldol condensation and hydrogenation. Conventional techniques for the production of 2EH utilize high pressure conditions and/or noble metals for the hydroformylation step, and elevated temperatures under modest hydrogen pressures in the hydrogenation step.

The current invention details a process to produce both 2EH and 2,4-diethyl-1-octanol (DEO) from 2-ethyl-1-hexene and 2,4-diethyl-1-octene, respectively. Both of these olefins can be selectively produced from abundant waste biomass sources including cellulose and hemicellulose. In effect, this technology allows for the renewable and sustainable synthesis of these branched alcohols. In contrast to established processes, 2EH and 2,4-diethyl-1-octanol (DEO) can be selectively synthesized in high yield under low temperature and pressure conditions using cheap and environmentally favorable catalysts. In addition, DEO represents a safer alternative to 2EH due to both its lower volatility and greater hydrophobicity.

The ability to produce plasticizers from renewable materials including waste biomass represents an opportunity to drastically reduce the carbon footprint of the Navy, while providing comparable performance to petroleum derived materials.

The disclosure describes an efficient, low-temperature process to convert well-defined olefin oligomers, particularly butene oligomers to branched chain alcohols suitable for use as precursors to plasticizers commonly used in industry. The olefin feedstocks can be conveniently and renewably produced from short chain alcohols.

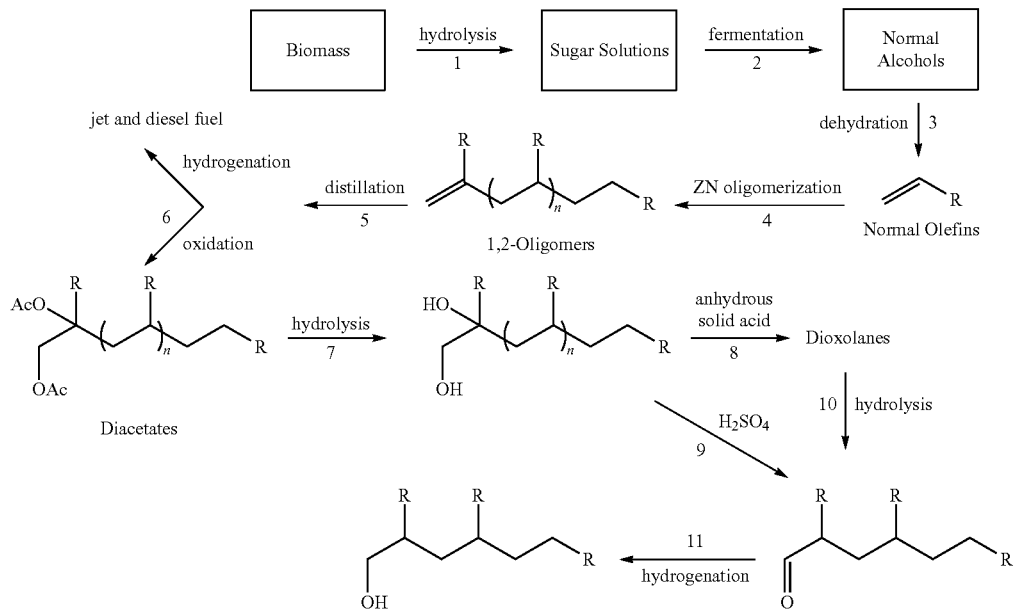

Scheme 1

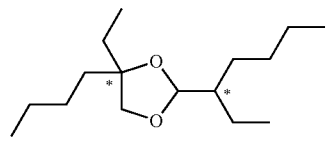

Example of a dioxolane, n = 0, R = Et

Embodiments of the invention describe the synthesis of industrially important branched chain alcohols from selected olefins derived from the synthesis of jet fuel from biobutene. The key steps of the process are:
1. Cellulosic, hemicellulosic, or lignocellulosic biomass is broken down by physical, chemical, or enzymatic methods to produce a sugar solution.
2. This sugar solution is fermented to produce n-butanol or other linear alcohols which are isolated by techniques including distillation, phase separation, and pervaporation.
3. The alcohols (butanol) are dehydrated with a catalyst to selectively produce normal olefins (1-butene).
4. The olefin (e.g. 1-butene) is oligomerized with a Ziegler Natta catalyst system to produce a series of 1,2-addition products (in the case of butene; 2-ethyl-1-hexene, 2,4-diethyl-1-octene, and 2,4,6-triethyl-1-decene).
5. The mixture of oligomers is fractionally distilled to isolate either pure or mixed solutions of oligomers (in the case of 1-butene, 2-ethyl-1-hexene and 2,4-diethyl-1-octene).
6. The oligomers are oxidized by various methods (e.g. $NaIO_4$, peracetic acid, MCPBA, or $OsO_4$) to produce pure compounds or mixtures of diacetates, acetate/alcohols, dials, dioxolanes and oxiranes.
7. The oxidized mixtures are allowed to react with $K_2CO_3$ or another hydrolysis reagent to yield the diol.
8. The product in 7 is dehydrated in the presence of an acid clay or other catalyst to yield a mixture of dioxolane isomers.
9. The product from steps 7 or 8 can be chemically modified with sulfuric acid to yield the aldehyde.
10. Alternatively, the product from step 8 can be hydrolyzed with dilute acid to produce a stoichiometric mixture of the aldehyde and the diol
11. The aldehyde can then be hydrogenated to yield a branched chain primary alcohol.
See Scheme 1 for a graphical representation of the steps above.

Steps 1-3 can be accomplished by known techniques. In addition, butene or other primary olefins derived from petroleum can be used in step 4. Internal olefins including 2-butene, 2-pentene, 2-hexene, and 3-hexene can also be used as described in U.S. Pat. No. 8,242,319 which is incorporated herein by reference.

Step 4 is conducted as described in patent application Ser. No. 12/511,796 filed Jul. 29, 2009. The amount of dimer, trimer, tetramer, etc. can be controlled by the ratio of MAO/Zr, with lower ratios resulting in the production of greater amounts of dimer. Thus the current invention can be utilized to convert excess dimer to 2EH, while heavier oligomers (trimer, tetramer, pentamer) are diverted to jet or diesel fuel. Alternatively, by significantly lowering the MAO/Zr ratio, dimer can be made selectively, allowing for a direct route to 2EH. Any catalyst that produces olefin oligomers through 1,2-addition can be utilized for the process. Either renewable or petroleum derived olefins, particularly propylene, 1-butene, 1-pentene, and 1-hexene can be used in this process.

Step 5: The oligomers are fractionally distilled to yield pure aliquots of specific molecules. In the case of butene, pure dimer (2-ethyl-1-hexene) and trimer (2,4-diethyl-1-octene) are isolated, The key oligomers for other olefins are: propylene [trimer (C9) and tetramer (C12)] pentene [dimer (C10)], 1-hexene [dimer (C12)].

Step 6: A pure oligomer or mixture of oligomers can be oxidized by a variety of methods in the presence of acetic acid or water to produce mixtures of diacetates, mixed acetate/alcohols, diols, dioxolanes and oxiranes. $NaIO_4$ and peracetic acid are effective oxidants, but other oxidants including $OsO_4$, $KMnO_4$, MCPBA, and other common peroxy acids can also be used.

Step 7: A base (e.g. $Na_2CO_3$, $K_2CO_3$, NaOH, KOH, LiOH) is used to hydrolyze the diacetate or acetate alcohols to diols.

Step 8: The products from step 7 are allowed to react with an acid catalyst or other dehydration catalyst. Examples include molecular sieves, zeolites, acid clays, transition metal catalysts, cation exchange resins, alumina, mineral acids, aluminum phosphate, etc. Water can be removed by distillation either directly or azeotropically by running the reaction in a suitable solvent. This results in the isolation of dioxolanes resulting from the reaction of an intermediate aldehyde and the diol.

Step 9: The product from step 7 or 8 is dehydrated with a concentrated mineral acid or selective heterogeneous catalyst to yield the aldehyde.

Step 10: Alternatively, the product from step 8 is hydrolyzed with a dilute acid solution to yield a stoichiometric mixture of the aldehyde and diol which can be separated by distillation.

Step 11: The aldehyde is catalytically converted to the alcohol by reaction under hydrogen pressure in the presence of a catalyst including a transition metal (Ni, Pd, Pt, and Cu).

EXPERIMENTAL

General Methods. All organometallic manipulations were carried out using standard Schlenk techniques under an atmosphere of purified nitrogen. 1-butene (CP grade) was stirred over $CaH_2$ and degassed prior to use. MAO (10% in toluene), $PtO_2$, peroxyacetic acid (32 wt. % in dilute acetic acid), 3-chloroperoxybenzoic acid (MCPBA 77%), lithium bromide (99+%), $Cp_2ZrCl_2$, $NaIO_4$, and glacial acetic acid were obtained from commercial suppliers and used as received. Raney nickel (2800) was washed with distilled water (3×) and 2-propanol (3×) and stored under 2-propanol. Butene oligomerization reactions were conducted in a 750 mL stainless steel reactor fitted with a glass insert. $^1H$ and $^{13}C$ NMR spectra were collected on a 300 MHz spectrometer in $CDCl_3$ and referenced to the residual solvent peaks ($^1H$, δ 7.27; $^{13}C$, δ 77.16). Selected compounds and mixtures were analyzed with a gas chromatography (GC) system equipped with an RTX-5MS 30-meter column. The GC inlet temperature was 250° C., the initial column temperature was 40° C. held at 3 min, and the temperature was increased at 10° C./min up to a final temperature of 350° C. A mass selective detector was used to help identify the sample components.

Example 1

2-ethyl-1-hexene. The compound was prepared by a modification of a recently reported procedure and was optimized for isolation of 2-ethyl-1-hexene. Utilizing Schlenk techniques, $Cp_2ZrCl_2$ (70 mg, 0.24 mmol) was dissolved in MAO solution (8.25 mL, 12.5 mmol) to yield a pale yellow solution which was stirred at ambient temperature for 1 h. The resulting golden colored solution was then stripped of solvent under reduced pressure (0.1 mm Hg) to give a yellow solid. Rigorously dry hexanes (10 mL), were added to the flask with vigorous stirring to form a pale yellow slurry that was then transferred via a syringe into the bomb. The bomb was then removed from the glovebox and packed in dry ice. 1-butene (375 mL, 4.22 mol) was condensed into the bomb which was sealed, placed on a stir plate, warmed to room temperature, and allowed to react for 48 h with stirring. The bomb was then opened and the catalyst quenched with water. The mixture was filtered through a short plug of alumina and the 2-ethyl-1-hexene isolated by fractional distillation using a 9-inch vacuum jacketed Vigreux column. This resulted in an isolated yield of 161 g (68%). The residual oligomer solution was set aside for later use (see below).

Example 2

1,2-diacetoxy-2-ethylhexane (Method 1). This compound was prepared through an adaptation of a recently published procedure. 2-ethyl-1-hexene (15.03 g, 134 mmol), $NaIO_4$ (10.49 g, 49 mmol), and LiBr (2.59 g, 30 mmol) were dissolved in 200 mL of glacial acetic acid and the mixture was heated at 95° C. for 15 hours. The resulting dark red solution was then extracted with EtOAc and the organic layer was washed with each of the following: saturated sodium thiosulfate, water, and aqueous $NaHCO_3$. The organic layer was then dried over $MgSO_4$ and the ethyl acetate removed under reduced pressure to yield a tan oil. The oil was a 2:1 mixture of 1,2-diacetoxy-2-ethylhexane and 2-ethyl-2-hydroxyhexyl acetate (yield: 20.2 g, 68%). $^1$H NMR of the major product ($CDCl_3$) δ: 0.88 (m, 6H), 1.28 (m, 4H), 1.52 (m, 4H), 2.08 (s, 3H), 2.10 (s, 3H), 3.99 (s, 2H). $^{13}$C NMR ($CDCl_3$) δ: 7.6, 14.0, 20.9, 23.2, 25.3, 28.9, 35.6, 69.2, 73.5, 171.1.

Example 3

1,2-diacetoxy-2-ethylhexane (Method 2). Peracetic acid solution (15 mL, 71 mmol) was added to a mixture of 2-ethyl-1-hexene (7.3 g, 65 mmol) and acetic acid (15 mL). The mixture was heated at 50° C. for 2 h and then 65° C. for an additional 2 h. After cooling to room temperature the mixture was neutralized with saturated $NaHCO_3$, extracted with ether, and washed several times with water. The organic layer was then dried over $MgSO_4$ and the ether removed to yield a clear oil (10.6 g, 82% based on the GC distribution: 80% 1,2-diaceto-2-ethylhexane and 20% dioxolanes).

Example 4

2-ethylhexane-1,2-diol (Method 1). 1,2-diacetoxy-2-ethylhexane (19.5 g, 85 mmol) was stirred with $K_2CO_3$ (28.0 g, 203 mmol) in 125 mL of MeOH at 50° C. for 15 h. The solvent was removed under reduced pressure and the residue was then extracted with EtOAc and washed with $H_2O$ and brine. The organic layer was dried with $MgSO_4$ and the EtOAc removed under reduced pressure to yield a tan oil (11.93 g, 96%). Simple vacuum distillation (0.1 Torr) provided an analytically pure, colorless oil. $^1$H NMR ($CDCl_3$) δ: 0.91 (m, 6H), 1.30 (m, 4H), 1.50 (m, 4H), 1.82 (s, 1H), 2.03 (s, 1H), 3.46 (s, 2H). $^{13}$C NMR ($CDCl_3$) δ: 7.7, 14.0, 23.2, 25.5, 28.3, 35.0, 67.8, 74.8. Anal. Calcd for $C_8H_{18}O_2$: C, 65.7; H, 12.4. Found: C, 65.3; H, 12.0.

Example 5

2-ethylhexane-1,2-diol (Method 2). Peracetic acid solution (15 mL, 71 mmol) was added to a mixture of 2-ethyl-1-hexene (7.3 g, 65 mmol) and 15 mL of $H_2O$. The mixture was heated at 50° C. for 2 h and then 65° C. for an additional 2 h. After cooling to room temperature the mixture was extracted with ether and washed several times with water. The organic layer was then dried over $MgSO_4$ and the ether removed to yield a colorless oil (7.5 g, 81% yield based on the GC distribution of diol and dioxolanes).

Example 6

Dehydration of 2-ethylhexan-1,2-diol (Nafion). 2-ethyl-1,2-hexanediol (2.20 g, 15 mmol) and Nafion SAC-13 (1.00 g) were heated to 175° C. for 6 h. The flask was equipped with a short path distillation column and a receiving flask, but no significant distillate was observed over the course of the reaction. The reaction mixture was decanted from the catalyst and analyzed by GC. 20% conversion of the diol to a mixture of four diasteriomeric dioxolanes was observed.

Example 7

Dehydration of 2-ethylhexan-1,2-diol (MMT-K10). 2-ethyl-1,2-hexanediol (5.01 g, 34.3 mmol) was stirred with MMT-K10 (1.8 g) in 50 mL of benzene at an oil bath temperature of 95° C. The water generated in the reaction was collected using a Dean-Stark trap. After 6 hours the mixture was cooled to room temperature and the MMT-K10 was removed by filtration. Removal of the benzene under reduced pressure yielded 3.74 g of a tan oil (85%). By GC-MS this procedure gave >95% conversion to a mixture of four diasteriomeric dioxolanes. The NMR spectra were extremely complex due to the overlap of peaks arising from the four isomers.

Example 8

2-ethylhexanal. A distillation apparatus was assembled consisting of a reaction flask connected by a short curved glass tube to a Schlenk type receiver. 2 mL of $H_2SO_4$ (9 M) was added to the reaction flask, followed by 2-ethyl-1,2-hexanediol (0.91 g, 6.2 mmol). The mixture was stirred at room temperature for five min and the reaction flask then placed in a 100° C. oil bath. The pressure in the apparatus was reduced by slowly opening the Schlenk flask to a high vacuum line until vigorous boiling of the reaction mixture was evident. The receiver flask was cooled in dry ice and the products distilled until the reaction mixture turned dark red-black. The system was periodically exposed to the vacuum line to maintain rapid boiling. The resulting distillate was extracted with ether, washed with aqueous $NaHCO_3$ and water and dried over $MgSO_4$. Removal of the ether under reduced pressure yielded 0.72 g (90%) of 2-ethylhexanal (confirmed by $^1$H NMR spectroscopy).

Example 9

5-ethyl-3-methylenenonane. The pot residue from the synthesis of 2-ethyl-1-hexene was fractionally distilled under nitrogen using a 9-inch vacuum jacketed Vigreux column. Product distilling between 185 and 200° C. was collected and represented >95% pure 5-ethyl-3-methylenenonane. Yield: 34 g, 14% (combined yield of 2-ethyl-1-hexene and 5-ethyl-3-methylenenonane—83%) $^1$H NMR (CDCl$_3$) δ 4.76 (s, 1H), 4.70 (s, 1H), 2.12-1.93 (m, 4H), 1.38-1.19 (m, 8H), 1.04 (t, 3H, J=7.4 Hz), 0.98-0.81 (m, 6H). $^{13}$CNMR (CDCl$_3$) δ: 150.7, 109.1, 41.3, 36.9, 32.8, 29.1, 28.6, 25.9, 23.3, 14.3, 12.5, 10.9. Anal. Calcd for C$_{12}$H$_{24}$: C, 85.63; H, 14.37. Found: C, 85.33; H, 14.55.

Example 10

Oxidation of 5-ethyl-3-methylenenonane (Method I). 7.5 g of 5-ethyl-3-methylenenonane (7.5 g, 45 mmol) was added to a peracetic acid solution (15 mL, 71 mmol) diluted in 15 mL of acetic acid. The mixture was heated to 50° C. for 2 h and 65° C. for an additional 2 h. After cooling to room temperature, the mixture was extracted with ether and washed with excess H$_2$O to yield a total of 8.4 g of colorless oil. The product was a complex mixture of diacetates, monoacetates, diols, and epoxides. Under similar conditions, 5-ethyl-3-methylenenonane (1.5 g, 8.9 mmol), peracetic acid solution (2.0 mL, 9.5 mmol) and 5 mL H$_2$O gave 1.6 g of product with a similar distribution. Treatment of the crude mixtures with K$_2$CO$_3$ in methanol at 50° C. did not change the product distribution significantly.

Example 11

2-ethyl-2-(2-ethylhexyl)oxirane/2,4-diethyloctane-1,2-diol (Method 2). In an adaptation of a published procedure, 5-ethyl-3-methylenenonane (1.4 g, 8.3 mmol) was dispersed in deionized water (50 mL), the flask was cooled to 0° C., and powdered m-chloroperoxybenzoic acid (2.04 g (77%), 9.1 mmol) was added in small portions over 5 min. The mixture was stirred for 8 h at room temperature and then 1.5 mL of H$_2$SO$_4$ (10%) was added and the flask left to stand for an additional 8 h. Solid NaOH was then added until all solids dissolved. The aqueous solution was saturated with NaCl and extracted with three 15 mL aliquots of ethyl acetate. The extracts were dried with MgSO$_4$ and the solvent removed under reduced pressure to give a colorless oil (yield: 1.25 g, 80%). The mixture consisted of diasteriomers of 2-ethyl-2-(2-ethylhexyl)oxirane and 2,4-diethyloctane-1,2-diol in a 4:1 ratio. $^1$H NMR of the diasteriomeric oxiranes (CDCl$_3$) δ: 2.59 (dd, 1H, J=4.9, 0.8 Hz), 2.52 (dd, 1H, J=4.9, 2.1 Hz), 1.70-1.49 (m, 3H), 1.45-1.15 (m, 11H), 0.94 (s, 1H, —OH), 0.91 (s, 1H, —OH), 0.92-0.79 (m, 8H). $^{13}$C NMR (CDCl$_3$) δ: 59.57, 59.54, 52.85, 52.81, 38.2 (br—overlap of two peaks), 35.8 (br—overlap of two peaks), 33.3, 33.0, 28.9, 28.8, 26.9 (br—overlap of two peaks), 26.5, 26.1, 23.17, 23.15, 14.22, 14.20, 10.79, 10.73, 8.94, 8.91.

Example 12

2,4-diethyloctanal. In a manner similar to that used for the synthesis of 2-ethylhexanal, 2,4-diethyloctanal was prepared from the mixture of 2-ethyl-2-(2-ethylhexyl)oxirane and 2,4-diethyloctane-1,2-diol (yield: 61%). $^1$H NMR (CDCl$_3$) δ: 9.55 (s, 1H, HC=O), 9.53 (s, 1H, HC=O), 2.32-2.19 (m, 1H), 1.77-1.42 (m, 3H), 1.42-1.13 (m, 10H), 1.03-0.79 (m, 9H). $^{13}$C NMR (CDCl$_3$) δ: 183.32 (broad—overlap of peaks HC=O), 45.15, 45.10, 37.0, 36.8, 36.05, 36.02, 33.0, 32.5, 28.7, 28.6, 26.1, 26.0, 25.9, 25.5, 23.20, 23.15, 14.2 (broad—overlap of peaks), 11.9 (broad overlap of peaks), 10.7, 10.4.

Example 13

2,4-diethyl-1-octanol. In an adaptation of a published procedure, Raney nickel (~1 g) was slurried in 2-propanol (15 mL) and one drop of concentrated HCl was added. The mixture was heated to reflux for 5 min and then cooled to room temperature. 2,4-diethyloctanal (0.70 g, 3.8 mmol) was added to the flask and the mixture was vigorously stirred and refluxed in air for two h. The flask was cooled to room temperature and the 2-propanol solution was decanted. The Raney nickel was washed with additional 2-propanol (2×10 mL) and the washings combined. Removal of the 2-propanol under reduced pressure gave a mixture of two diasteriomers of 2,4-diethyl-1-octanol as a colorless oil (0.62 g, 88%). $^1$H NMR (CDCl$_3$) δ: 3.59-3.44 (m, 2H), 1.54-1.10 (m, 15H), 0.95-0.80 (m, 9H). $^{13}$C NMR (CDCl$_3$) δ: 65.41, 65.38, 39.38, 39.37, 36.21, 36.19, 34.80, 34.77, 33.09, 33.05, 28.78, 28.73, 26.07, 26.01, 23.7, 23.6, 23.1 (broad—overlap of peaks), 14.0 (broad—overlap of peaks), 10.83, 10.82, 10.54, 10.48. Anal. Calcd for C$_{12}$H$_{26}$O: C, 77.35; H, 14.06. Found: C, 77.61; H, 13.59.

Embodiments of the invention generally relate to a method for manufacturing jet and diesel fuels including, oligomerizing at least one olefin with at least one Ziegler Natta catalyst to produce 1,2-oligomers, and fractionally distilling and hydrogenating 1,2-oligomers to produce jet and diesel fuels. Another embodiment of the invention includes jet and/or diesel fuels produced by the methods above.

Yet another embodiment of the invention relates to a method for manufacturing renewable plasticizers including, oligomerizing at least one olefin with at least one Ziegler Natta catalyst to produce 1,2-oligomers, fractionally distilling and oxidizing 1,2-oligomers with an oxidizing agent to produce a first mixture of at least one of diacetates, acetate/alcohols, diols, dioxolanes or oxiranes, hydrolyzing the first mixture with at least one hydrolysis reagent or weak base to produce diols, dehydrating the diols with a dehydration or acid catalyst to produce aldehydes or dioxolane isomers, where the dioxolane isomers are either: hydrolyzed with at least one dilute acid to produce a stoichiometric mixture of aldehydes/diols, or dehydrated with at least one mineral acid or selective heterogeneous catalyst to produce aldehydes, hydrogenating the aldehydes with at least one hydrogenation catalyst under hydrogen pressure to produce branched chain primary alcohols. Still yet another embodiment of the invention is renewable plasticizers produced by the methods above.

Embodiments of the invention include at least one olefin selected from the group consisting of propylene, 1-butene, 1-pentene, 1-hexene, and any combination thereof. In embodiments, at least one olefin is selected from the group consisting of propylene, butenes, pentenes, hexenes, and any combination thereof. In other embodiments the 1,2-oligomers are selected from the group consisting of 2-ethyl-1-hexene, 2,4-diethyl-1-octene, and 2,4,6-triethyl-1-decene. In yet other embodiments the 1,2-oligomers are selected from the group consisting of 2-methylpent-1-ene, 2,4-dimethylhept-1-ene, 2,4,6-trimethylnon-1-ene, 4-methylenenonane, and 5-methylenundecane.

In embodiments, the oxidizing agent is selected from the group consisting of $NaIO_4$/LiBr, peracetic acid, MCPBA, $OsO_4$, $KMnO_4$, other peroxy acids, and any combination thereof. In embodiments, at least one hydrolysis reagent or base is selected from the group consisting of $K_2CO_3$, $Na_2CO_3$, NaOH, KOH, LiOH, and any combination thereof. In embodiments, the diol(s) is 2-ethylhexan-1,2-diol. In other embodiments, the diol(s) is 2,4-diethyloctan-1,2-diol. Yet in other embodiments, the diol(s) is 2,4,6-triethyldecan-1,2-diol. In other embodiments, the dehydration or acid catalyst is selected from the group consisting of acidic clays, MMT-K10, molecular sieves, zeolites, transition metal catalysts, cation exchange resins, alumina, mineral acids, aluminum phosphate and any combination thereof. In embodiments, the dioxolane isomers are selected from the group consisting of 4-butyl-4-ethyl-2-(hept-3-yl)-1,3-dioxolane, 4-ethyl-4-(2-ethylhexyl)-2-(5-ethylnonan-3-yl)-1,3-dioxolane, 4-(2,4-diethyloctyl)-2-(5,7-diethylundecane-3-yl)-4-ethyl-1,3-dioxolane and any combination thereof. In embodiments, the oxirane isomers are selected from 2-butyl-2-ethyloxirane, 2-ethyl-2-(2-ethylhexyl)oxirane, 2-(2,4-diethyloctyl)-2-ethyloxirane, and any combination thereof.

Embodiments of the invention include at least one dilute mineral acid selected from the group consisting of $H_2SO_4$, HCl, or other common acids, and any combination thereof. In embodiments, the aldehyde(s) is 2-ethylhexanal. In other embodiments, the aldehyde(s) is 2,4-diethyloctanal. In yet other embodiments, the aldehyde(s) is 2,4,6-triethyloctanal. Embodiments of the invention include at least one hydrogenating catalyst that includes a metal selected from the group consisting of, Pt, Pd, Ni, Cu, and any combination thereof.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is to be understood that the foregoing is exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:
1. A method for manufacturing renewable plasticizer alcohols, comprising:
oligomerizing at least one olefin with at least one Ziegler Natta catalyst to produce 1,2-oligomers, wherein said at least one olefin is selected from the group consisting of propylene, 1-butene, 1-pentene, 1-hexene, and any combination thereof;
fractionally distilling and oxidizing said 1,2-oligomers with an oxidizing agent to produce a first mixture of at least one of diacetates, acetate/alcohols, diols, dioxolanes or oxiranes;
hydrolyzing said first mixture with at least one hydrolysis reagent or weak base to produce diols and either;
dehydrating said diols with at least one dehydrating catalyst to produce aldehydes; or
dehydrating said diols with a heterogeneous dehydration catalyst to produce dioxolane isomers, wherein said dioxolane isomers are hydrolyzed with at least one dilute aqueous acid to produce a stoichiometric mixture of aldehydes/diols;
separating said aldehydes by fractional distillation with concomitant recycling of said diols; and
hydrogenating said aldehydes with at least one hydrogenating catalyst under hydrogen pressure to produce branched chain primary alcohols.

2. A method for manufacturing renewable plasticizer alcohols, comprising:
oligomerizing at least one olefin with at least one Ziegler Natta catalyst to produce 1,2-oligomers, wherein said 1,2-oligomers are selected from the group consisting of 2-ethyl-1-hexene, 2,4-diethyl-1-octene, and 2,4,6-triethyl-1-decene, and any combination thereof;
fractionally distilling and oxidizing said 1,2-oligomers with an oxidizing agent to produce a first mixture of at least one of diacetates, acetate/alcohols, diols, dioxolanes or oxiranes;
hydrolyzing said first mixture with at least one hydrolysis reagent or weak base to produce diols and either;
dehydrating said diols with at least one dehydrating catalyst to produce aldehydes; or
dehydrating said diols with a heterogeneous dehydration catalyst to produce dioxolane isomers, wherein said dioxolane isomers are hydrolyzed with at least one dilute aqueous acid to produce a stoichiometric mixture of aldehydes/diols;
separating said aldehydes by fractional distillation with concomitant recycling of said diols; and
hydrogenating said aldehydes with at least one hydrogenating catalyst under hydrogen pressure to produce branched chain primary alcohols.

3. The method according to claim 1, wherein said oxidizing agent is selected from the group consisting of $NaIO_4$/LiBr, peracetic acid, MCPBA, $OsO_4$, $KMnO_4$, other peroxyacids, and any combination thereof.

4. The method according to claim 1, wherein said at least one hydrolysis reagent or base is selected from the group consisting of $K_2CO_3$, $Na_2CO_3$, NaOH, KOH, LiOH, and any combination thereof.

5. The method according to claim 1, wherein said diol is 2-ethylhexan-1,2-diol.

6. The method according to claim 1, wherein said diol is 2,4-diethyloctan-1,2-diol.

7. The method according to claim 1, wherein said diol is 2,4,6-triethyldecan-1,2-diol.

8. The method according to claim 1, wherein said heterogeneous dehydration catalyst is selected from the group consisting of acid clays, MMT-K10, molecular sieves, zeolites, transition metal catalysts, cation exchange resins, alumina, mineral acids, aluminum phosphate, and any combination thereof.

9. The method according to claim 1, wherein said dioxolane isomers are selected from the group consisting of 4-butyl-4-ethyl-2-(hept-3-yl)-1,3-dioxolane, 4-ethyl-4-(2-ethylhexyl)-2-(5-ethylnonan-3-yl)-1,3-dioxolane, 4-(2,4-diethyloctyl)-2-(5,7-diethylundecane-3-yl)-4-ethyl-1,3-dioxolane, and any combination thereof.

10. The method according to claim 1, wherein said oxiranes are selected from the group consisting of 2-butyl-2-ethyloxirane, 2-ethyl-2-(2-ethylhexyl)oxirane, diethyloctyl)-2-ethyloxirane, and any combination thereof.

11. The method according to claim 1, wherein said at least one hydrolyzed acid is selected from the group consisting of $H_2SO_4$, HCl, mineral acids, and any combination thereof.

12. The method according to claim 1, wherein said aldehyde is 2-ethylhexanal.

13. The method according to claim 1, wherein said aldehyde is 2,4-diethyloctanal.

14. The method according to claim 1, wherein said aldehyde is 2,4,6-triethyldecanal.

15. The method according to claim 1, wherein said at least one hydrogenating catalyst includes a metal selected from the group consisting of Pt, Pd, Ni, Cu, and any combination thereof.

16. Renewable plasticizers synthesized from branched chain alcohols that are produced by the methods of claim 1.

17. The method of claim 1, wherein said process is a continuous biphasic process for oxidizing olefin oligomers.

* * * * *